United States Patent
Braun et al.

[11] Patent Number: 6,162,244
[45] Date of Patent: Dec. 19, 2000

[54] LAYERED STENT

[75] Inventors: Michael Braun, Backnang; Armin Singvogel, Remseck, both of Germany; Walter Klepetko, Vienna, Austria; Christoph Bolliger, Oberwil, Switzerland; Lutz Freitag, Hemer, Germany

[73] Assignee: Willy Ruesch AG, Kernen-Rommelshausen

[21] Appl. No.: 09/155,363

[22] PCT Filed: Mar. 27, 1997

[86] PCT No.: PCT/DE97/00649

§ 371 Date: Sep. 23, 1998

§ 102(e) Date: Sep. 23, 1998

[87] PCT Pub. No.: WO97/36556

PCT Pub. Date: Oct. 9, 1997

[30] Foreign Application Priority Data

Mar. 29, 1996 [DE] Germany .......................... 196 12 615
Feb. 26, 1997 [DE] Germany .......................... 197 07 642

[51] Int. Cl.⁷ ...................................................... A61F 2/06
[52] U.S. Cl. ....................... 623/1.12; 623/1.15; 623/1.44; 623/1.22
[58] Field of Search ................................. 623/1, 12, 1.15, 623/1.27, 1.32, 1.44

[56] References Cited

U.S. PATENT DOCUMENTS

| | | | |
|---|---|---|---|
| 5,059,169 | 10/1991 | Zilber | 604/8 |
| 5,123,917 | 6/1992 | Lee | 623/1 |
| 5,356,423 | 10/1994 | Tihon et al. | 606/194 |
| 5,383,928 | 1/1995 | Scott et al. | 623/1 |
| 5,788,626 | 8/1998 | Thompson | 623/1 |
| 5,869,127 | 2/1999 | Zhong | 427/2 |
| 5,879,380 | 3/1999 | Kalmann et al. | 623/1 |
| 5,948,018 | 9/1999 | Dereume et al. | 623/1 |

FOREIGN PATENT DOCUMENTS

| | | |
|---|---|---|
| 579523 | 1/1994 | European Pat. Off. . |
| 621016 | 10/1994 | European Pat. Off. . |
| 622059 | 11/1994 | European Pat. Off. . |
| 679372 | 11/1995 | European Pat. Off. . |
| 696446 | 2/1996 | European Pat. Off. . |
| 696447 | 2/1996 | European Pat. Off. . |
| 1766921 | 1/1970 | Germany . |
| 4022956 | 2/1992 | Germany . |
| 9206734 | 4/1992 | WIPO . |
| 9306781 | 4/1993 | WIPO . |
| 9505132 | 2/1995 | WIPO . |
| 9517859 | 7/1995 | WIPO . |
| 9600103 | 1/1996 | WIPO . |

*Primary Examiner*—David H. Willse
*Assistant Examiner*—Suzette J. Jackson
*Attorney, Agent, or Firm*—Paul Vincent

[57] ABSTRACT

The invention concerns a stent 1 for the bracing and/or holding-open of a body cavity having a tube 2 made from an elastic material, a tubular weave 3 comprising filaments 5 seating in close adjacency to the outer surface of the tube 2 as well as a coating 4 applied to the outer surface of the tube 2 which attaches the weave 3 to the outer surface of the tube 2. The coating 4 is adapted to have a structured outer surface dominated by the weave 3. The stent 1 in accordance with the invention can be produced economically with adjustable restoring forces and facilitates a secure placing within the body cavity. Means for preventing drifting within the body cavity can also be introduced onto outer surface of the stent.

23 Claims, 5 Drawing Sheets

LAYERED STENT

BACKGROUND OF THE INVENTION

The invention concerns a stent for the splinting and/or holding-open of a body cavity, in particular, an organ cavity.

DE 176 69 21 describes a stent configuration for the splinting and holding-open of a body cavity. The conventional configuration has a tubular self-expanding network made from a plurality of mutually woven filaments. In accordance with an embodiment of DE 176 6921, the stent is configured as a reinforced tube, wherein the network is firmly embedded within the tube. In the event that the tube is fashioned from a material which is gentle to tissue, for example made from a plastic, a stent device which is suitable for splinting or holding-open of an organ cavity results. Since the network is completely embedded within the walls of the tube, the outer surface of the tube is smooth and therefore gentle to tissue if the tube is made from a material which is likewise gentle to tissue. However, the tube can become displaced relative to a predetermined position within the organ cavity.

In contrast thereto, it is the purpose of the present invention to present a stent of the above mentioned kind which is economical to produce and which facilitates a secure location within an organ cavity or body cavity, which is gentle to tissue, and which facilitates a permanent and stable positioning.

SUMMARY OF THE INVENTION

This purpose is achieved with a stent having a tube made from elastic material, a tubular weave made from filaments firmly seating on the outer surface of the tube, and a coating covering both the weave as well as the outer surface of the tube and holding the weave on the outer surface of the tube, the coating having a structured outer surface dominated by the weave, wherein the diameter of the filaments forming the weave is larger than the thickness of the coating.

The formation of the stent in accordance with the invention as a composite product among three components having an inner tube, a tubular weave securely seated thereon and a coating disposed on the outer surface of the tube guarantees the production of a stent which is not only economical to manufacture but also facilitates a gentle and secure location within e.g. an organ cavity. The outer coating serves for fixing the weave on the outer surface of the tube, wherein the restoring forces (expansion of the stent from an elongated tensioned stent having a smaller diameter into a state of the stent having a larger diameter and therefore an enlarged lumen) is determined by the cooperation between the elastic properties of the tube and the weave. The coating is configured in such a fashion that a structured outer surface of the stent results which is dominated by the structure of the weave. In this manner, in contrast to the conventional stent, the stent in accordance with the invention has a structured surface which guarantees a secure holding within the body cavity. The choice of material for the stent, in particular material of the weave, can be used to adjust the restoring forces of the stent. In this manner, a more economical stent is produced which nevertheless guarantees secure location within the body cavity. The coating is kept sufficiently thin so that the structure of the filaments leads to a corrugated surface for the stent in individual areal sections. This structured surface improves secure location and holding of the stent permanently in position within the body cavity.

Further advantages result when the weave is self-expanding. In this manner, the restoring forces of the stent can also be adjusted through choice of a suitable weave and do not only result from the material properties of the tube.

In a preferred embodiment of the invention, the filaments have a round cross section. This measure has the advantage that conventional wire material can be used as filaments forming a weave. In addition, the simple structuring caused by a filament having a rounded cross section is sufficient to give a stent a prominent surface structure.

It is advantageous when the filament comprises polyester, kevlar, fiber glass, and/or metal or is made from such material. Polyester has the advantage that it is a well-known material having good processing characteristics and is suitable for creating a stable joining of the tube and the coating. The choice of filament material, for example polyester or kevlar influences the restoring forces of the stent. For example, kevlar is stiffer than polyester and serves to create a stent with stronger restoring forces. Use of fiber glass further expands possibilities for adjusting the restoring force. Metallic filaments lead to strongly reenforced stent structures and facilitate positioning and locating using X-ray investigations.

In an improvement in this embodiment, the filaments contain a mixture of fiber glass and metal. This measure has the advantage that the restoring forces can be adjusted while simultaneously allowing the position of the stent to be checked using X-ray radiation.

It is, in general, advantageous if the filaments are impervious to X-rays. This has the advantage that, independent of whether or not the restoring forces are defined by polyester, kevlar or metal, it is nevertheless possible to check the location of the stent using X-ray radiation.

In an advantageous improvement of this embodiment, the metallic powder or metallic pieces, for example of tungsten, are in the tube or in the coating. This measure has the advantage that the stent becomes "visible" through X-ray investigations not only when the filaments e.g. are made from metal, but also through metallic pieces imbedded into the stent to achieve an improved imperviousness to X-rays. In this manner, the choice of filament material can influence the restoring forces of the stent in an expanded final state and, independent thereof, the placing of the stent can be checked using X-ray radiation.

It is particularly advantageous when the tube and/or the coating includes silicon. This has the advantage that silicon is a particularly simple material to work and has properties which are gentle to tissue.

It is advantageous when the filaments have firmly fixed, protected ends. This has the advantage that filament ends cannot damage the tissue of a body cavity and that the structural stability of the stent in the end regions is improved in a defined manner. The weave can not fan out in the outer region.

In an improvement in this embodiment, the neighbouring filament ends are pairwise connected to each other. This has the advantage that the filament ends are captured and can not spread out freely.

In a particular embodiment of this improvement, the neighboring filament ends are connected to each other by means of a covering cap. This covering cap can be a tube or cover-like object. This has the advantage that a relatively simple mechanical construction, namely the covering cap, leads to reliable protection and localization of the filament ends.

In another embodiment of this improvement, the neighbouring filament ends are each captured within a common filament tube. The tube protects the ends of the filament and holds the ends of at least two filaments together.

It is, however, also possible to weld the filament ends together e.g. using ultrasound welding. This measure has the advantage that no additional material is necessary to guarantee a secure localization and protection of the filament ends.

It is also possible to firmly glue the filament ends to the silicon tube and to secure their location with a silicon coating (film). The crossing points at the ends can be knotted or wrapped using e.g. a silk thread. The combination of the inner tube and the covering cap has the advantage that the ends do not become loose when the stent is stretched. It is also possible to mark the ends with color to improve recognition of the stent ends when the stent is in the body. The inner surfaces of the stent can be structured in such a manner that a good and permanent moistening and transport of fluid and/or cell tissue is possible.

The tube preferentially has a fold-over extending over the filament ends. This has the advantage that the tube and the filament ends cooperate to captured the filament ends without having to produce additional material connections.

In a preferred embodiment, the stent has raised sections protruding beyond the structured outer surface.

This has the advantage that the stent, in addition to the structured outer surface, has means which guarantee an additional stationary positioning of the stent in the body cavity. The raised portions can be arbitrarily distributed over the outer peripheral surface of the stent and push over an area into the neightoring tissue or become anchored therein so that the position of the stent is additionally secured.

In an additional configuration of the invention, the raised portions are formed by free ends of filament pieces which are at least sectionwise proximate or parallel to the filaments forming the weave.

This has the advantage that, in order to produce such raised portions, only a single second filament thread is necessary which e.g. can extend parallel to the filament threads building the weave. This second filament thread should not influence the weave structure or stability and is separated after the desired sectional length is achieved. The resulting free ends are bent to protrude beyond the outer surface of the stent so that an outer surface is produced having a plurality of hooks which can penetrate into the surrounding tissue.

In an additional configuration of the stent in accordance with the invention, the raised portions are formed by anchors which, in the elongated state of the stent, seat flatly on the outer surface of the stent with a first end being attached in a position-stable fashion to the outer surface of the stent and a second free end, in an expanded state of the stent, being separated from the outer surface of the stent.

This has the advantage that such an anchor can also be fashioned retroactively on a structured outer surface of a stent. The anchors unfold when the stent is expanded and thereby penetrate into the bordering tissue. In the elongated state of a stent these anchors are flat at the outer surface of a stent so that placement of the stent is not rendered more difficult by means of these anchors.

In an additional embodiment of a stent in accordance with the invention, the filaments forming the weave have differing separations from each other and/or the filaments have differing diameters.

Variation of the type of weave and/or the grid size as well as of the thicknesses of the individual filament threads allows for adjustment of various restoring forces in a stent so that, in dependance on the size and properties of a position in a body cavity, the most suitable stent can be chosen. This stent therefore has a desired lumen expansion in the associated body cavity which is secured in a permanent fashion to rule out an unintentional migration of the stent.

In an additional embodiment the stent weave has differing contours in an axial and/or radial direction so that the adjustment force within the stent can be additionally varied in dependance on the axial position. Differing shapes of the weave can be produced using thermal deformation.

It is particularly advantageous when the stent is configured in such a fashion that it can be introduced into a body cavity using an application device. This has the is advantage that placement of the stent is simplified and reproduceable methods can be developed for placing the stent in accordance with the invention.

In an improvement of this embodiment, the application device has a capture and displacement device as well as an application bushing and a conical plug. This has the advantage that the stent is not only introduced into a body cavity using this application device, rather can also be positioned using this device. The conical plug serves for simplified handling in the application bushing.

In an improvement of this embodiment the capturing and displacement device has a spread-out capture basket made from a plastic or metallic weave. This has the advantage that the capture and displacement device can securely capture the stent and, after the stent is held folded together within the application bushing, can free same. The capture and displacement device is configured and dimensioned in such a manner that it can be displaced into the lumen of the application bushing.

If silicon is worked into the weave of the capturing basket, the capturing basket can slide easily against the surface of application bushing and/or of the stent. Coatings made from teflon or polyethylene also reduce friction. This guarantees a secure and simplified removal of the capture and displacement device from the stent which it engages.

It is advantageous when the capture and displacement device has a lumen. This has the advantage that the lumen of the capture and displacement device is suitable to guarantee observation of placement of the stent within a body cavity using optical means.

In an advantageous improvement, the capture and displacement device supports the stent when a section of the free end of the displacement device projects into the stent lumen. Small stent sizes <10 mm inner diameter can not be damaged during displacement out of the application bushing, since they are supported from the inside. An additional utilization of lubricant in the outer region of the stent is possible so that the friction between the inner surface of the application bushing and the outer surface of the stent is reduced.

In order to separate the stent from the capturing basket, the stent is not completely pulled into the application bushing. A conical plug is then used to fix the stent in the application bushing and the capture basket is pulled out. The protruding weaving can then be gently introduced into the application bushing e.g. with the assistance of the back side of the conical plug. If the conical plug were not used, deformation of and damage to the stent, in particular with sizes less than 10 mm inner diameter, could occur.

The capture device and application bushing can be fashioned in such a manner that both objects can be produced with low wall thicknesses. The application bushing then has a wall thickness which is sufficiently thin that it must be stabilized by the capture device.

The choice of materials can facilitate a very high degree of flexibility. This has the advantage that a secure and simple implantation of the stent is guaranteed in a manner which is gentle to surrounding bodies.

The invention also provides a method for introducing the stent, wherein the stent is pulled into the lumen of the application bushing using the conically widened end of the capture and displacement device, the stent is fixed using the conical plug within the lumen of the application bushing, the capture and displacement device is separated from the stent and pulled out of the lumen of the application bushing, the conical plug is separated from the application bushing, the capture and displacement device is reversed and inserted again into the lumen of the application bushing, optical means can be displaced through the lumen of the capture and displacement device, the application bushing is introduced into the hollow body, and the stent is pushed out of the application bushing using the capture and displacement device and placed within the body cavity. This has the advantage that the stent can be initially captured within the application bushing and held in a collapsed state in a simple manner using the application device. The capture and displacement device is not only used to pull the stent into the application bushing, rather also to push the stent out of the application bushing into the body cavity. The capture and displacement device thereby has an end having a capture device and an opposite end adapted to displace the stent out of the application device and into the body cavity.

A method for the production of a stent in accordance with the invention has the following steps: the weave is introduced on the outer surface of the tube in a firmly seating fashion and, subsequent thereto, the tube and the weave are dipped into a fluid, for example silicon. This fluid solidifies and forms the coating.

All free ends of the weave can also be welded to each other and additionally protected by means of a glue layer. If the glue layer contains barium sulfide, then the end of the stent generates X-ray shadows.

This has the advantage that the stent in accordance with the invention is very simple to produce.

BRIEF DESCRIPTION OF THE DRAWING

Additional advantages of the invention result from the description and the drawing. The above mentioned features and those to be described further below can be utilized in accordance with the invention individually or collectively in arbitrary combination. The embodiments shown and described are not to be considered exhaustive enumeration, rather have exemplary character only for illustrating the invention.

FIG. 4b shows an application device in accordance with

FIG. 4a having an inserted stent and conical plug;

FIG. 4c shows an application device having a capture and displacement device turned with respect to FIG. 4a;

DESCRIPTION OF THE PREFERRED EMBODIMENT

The figures are, in part, highly schematic to emphasize the features pertinent to the invention. The dimensions shown in the figures are only exemplary and are not to be taken to scale.

Figure 1A:
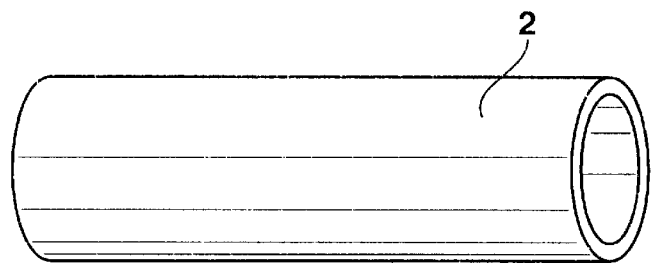
FIG. 1a shows a tube forming the basis of the stent.
Figure 1B:
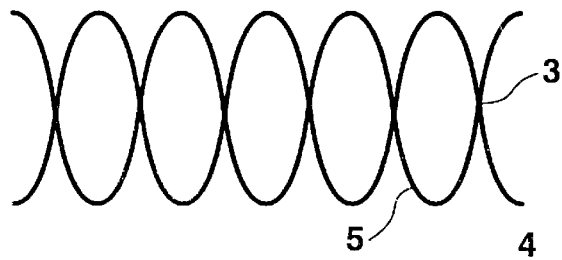
FIG. 1b shows a weave forming the basis of the stent.
Figure 1C:
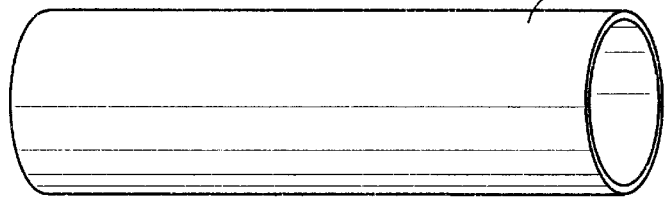
FIG. 1c shows a layer forming the basis of the stent in accordance with the invention.
Figure 1D:
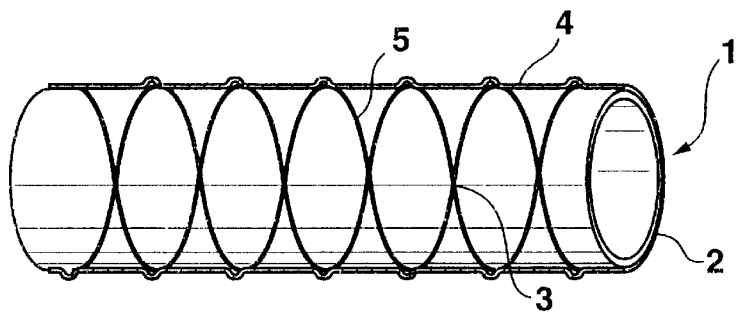
FIG. 1d is a schematic representation of the composition forming the stent in accordance with the invention comprising a tube, a weave and a coating.

FIGS. 1a–1d illustrate the construction of the stent 1 in accordance with the invention. The stent 1 consists essentially of a tube 2 (see FIG. 1a) made from elastic material, a tubular weave 3 tightly seating on the outer surface of the tube 2 (see FIG. 1b) and woven together from a plurality of filaments 5, as well as a coating 4 (FIG. 1c) introduced onto the outer surface of the tube 2. FIG. 1d shows the stent 1 in the constructed state. The inner tube 2 has a smooth inner surface and is strengthened through integration with the weaving 3 comprising the filaments 5, wherein the tubular weaving 3 and the inner tube 2 are joined by means of the coating 4. In accordance with FIG. 1d, the coating 4 is constructed in such a fashion that the prominent structure caused by the filaments 5 on the outer surface of the tube 2 projects through the coating 4 to lead to a structured outer surface of the coating 4.

Figure 2:
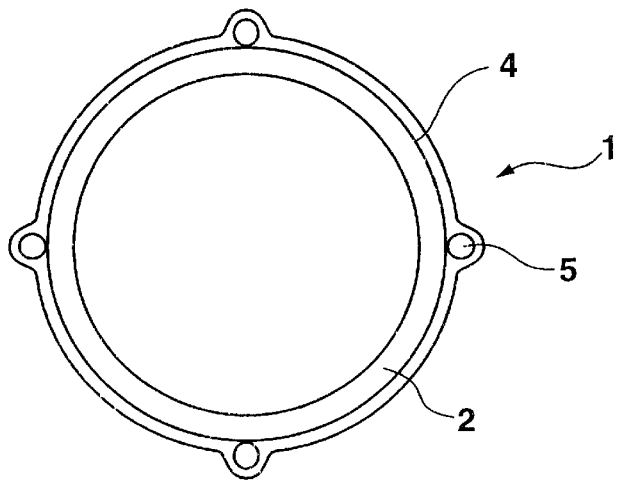
FIG. 2 shows a schematic cross section or end view of the stent of the invention in accordance with FIG. 1d.

FIG. 2 shows a schematic cross section or end view of the stent in accordance with the invention. The inner tube 2 as well as the weave 3, comprising the filaments 5 and tightly seating on the outer surface of the inner tube 2, are bonded together by means of the relatively thin coating 4. In the embodiment in accordance with FIG. 2, the stent 1 has a structured outer surface dominated by the filaments 5 of rounded cross section on the outer surface of the tube 2. The coating 4 is thereby sufficiently thin that the spaces between the filaments 5 are not completely filled-up, wherein the structure dominated by the filaments 5 at the outer surface of the tube 2 is simply covered in a sealed fashion using the coating 4.

Figure 3A:
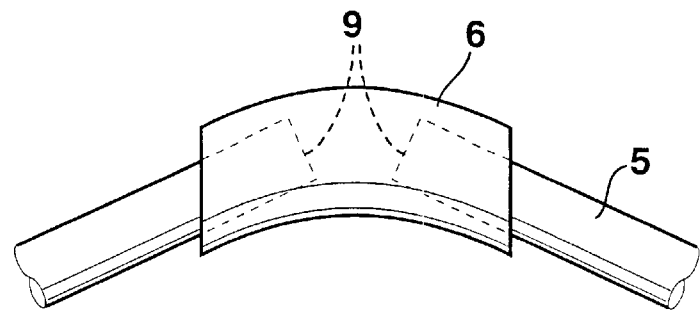
FIG. 3a shows an embodiment in accordance with the invention of capturing free filament ends using a cover cap.
Figure 3B:
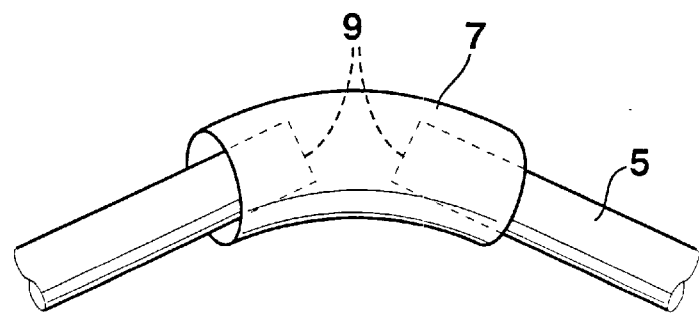
FIG. 3b shows an additional embodiment in accordance with the invention of captured filament ends using a filament tube.
Figure 3C:
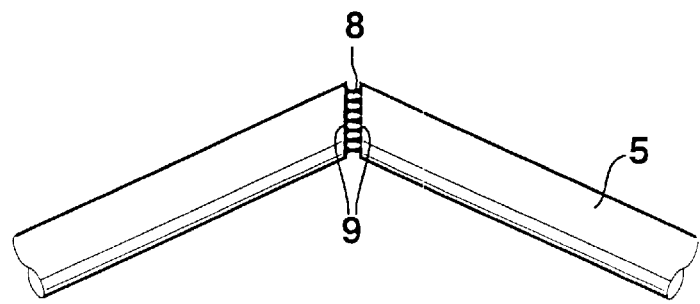
FIG. 3c shows an embodiment having welded filament ends.
Figure 3D:
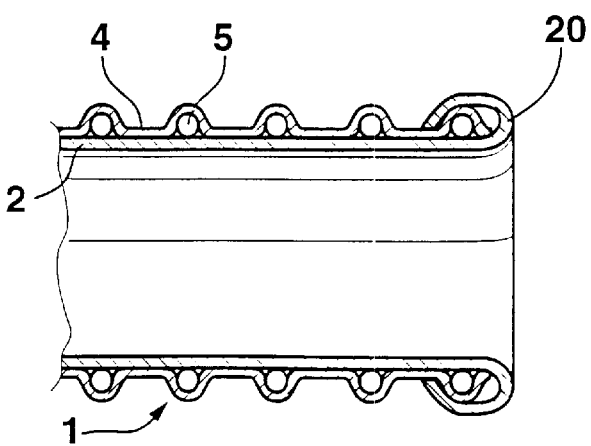
FIG. 3d shows a folding-over of the tube to effect capture of the filament ends.

The embodiments in accordance with FIGS. 3a–3d show different ways of holding the filament ends 9 together. In FIG. 3a, the ends 9 of the filaments 5 are connected to each other in a protected fashion using a cover cap 6. In accordance with FIG. 3b, the ends 9 of the filaments 5 are each connected to each other by means of a common filament tube 7. The free ends 9 of the filament 5 in accordance with FIG. 3c are held together and captured by means of a weldment 8. In accordance with FIG. 3d, it is also possible to capture the free ends of the filament 5 by means of a folding-over 20 of the inner tube 2.

Figure 4A:
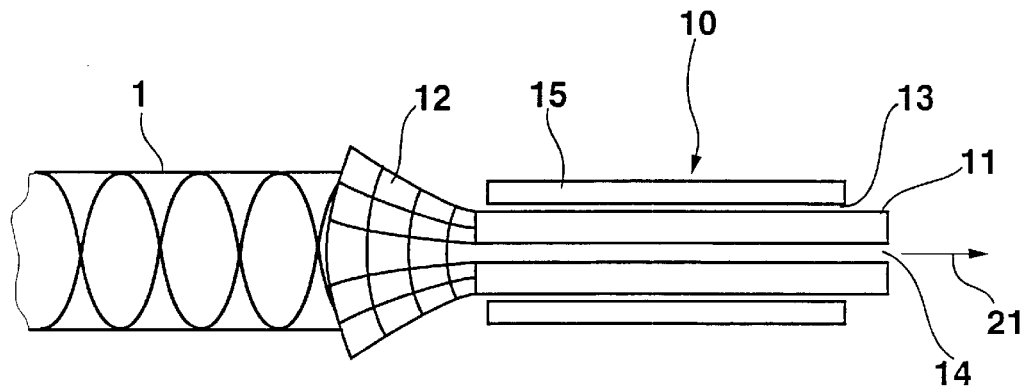
FIG. 4a shows an application device for placing the stent in accordance with the invention.
Figure 4B:
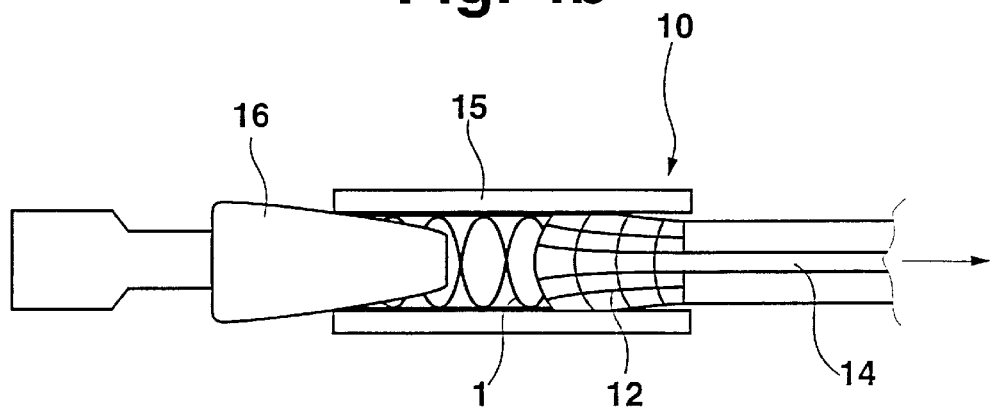

FIGS. 4a and 4b show an application device 10 which is suitable for introducing the stent 1 into a body cavity. The application device 10 in accordance with FIGS. 4a and 4b consists essentially of an outer application bushing 15 as well as an inner capture and displacement device 11. The inner capture and displacement device 11 has a spread-out capture device 12 at one end and is configured smoothly at the end opposite to the capture device 12. In addition, the capture and displacement device 11 has a lumen 14. In FIG. 4a, the stent 1 is pulled into the application device 10 in the direction of arrow 21 using the spread-out end of the capture device 12. The outer diameter of the capture and displacement device 11 is thereby dimensioned in such a fashion that it can be displaced within a lumen 13 of the application bushing 15. In accordance with FIG. 4c, a stent 1 which is already captured using the capture and displacement device 11 is displaced in the direction of arrow 22 out of the application bushing 15 and positioned within a body cavity.

Figure 4C:
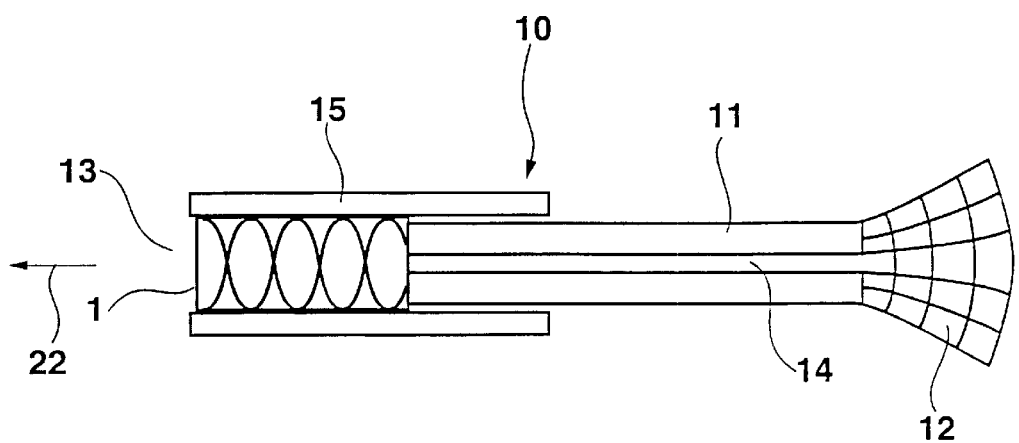

In order to utilize the application device in accordance with FIGS. 4a, 4b and 4c, the stent is initially pulled into the application bushing 15 in accordance with FIG. 4a by means of the spread-out end 12 of the capture and displacement device 11. After the stent 1 is completely within the application bushing 15 in accordance with FIG. 4b, the stent 1 is positioned within the lumen 13 of the application bushing 15 by means of the conical plug 16. A guided motion of the capture device 12 in the direction of arrow 21 then frees the stent 1. The conical plug 16 is removed from the application bushing 15 and the capture and displacement device 11 is pulled out of the application bushing 15, turned around and once more inserted into the application bushing 15 at its other end (see FIG. 4c). Optical observation of the placing of the stent 1 is facilitated by an instrument which can be guided through a lumen 14. The application device 10 is subsequently placed and situated within the body cavity through displacement of the capture and displacement device 11.

Figure 5:
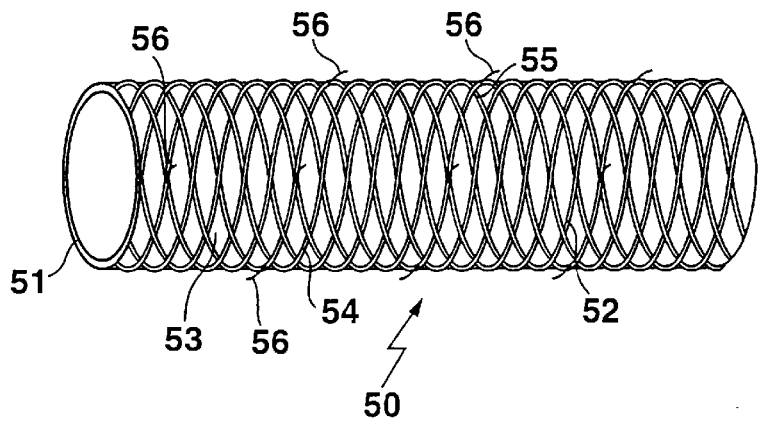
FIG. 5 shows a stent having raised portions on the outer peripheral surface formed by free ends of filament pieces.

FIG. 5 shows a stent 50 which is formed from a tube 51, a weave 52 and a coating 53. In addition to filament threads 54 from which the weave 52 is produced, a second filament thread 55 is adjacent to the threads 54 and is interrupted in sections, the free ends 56 of which protrude above the weave 52 and the coating 53. The free ends 56 build hooks for tissue adjacent to the outer surface of the stent.

Figure 6:
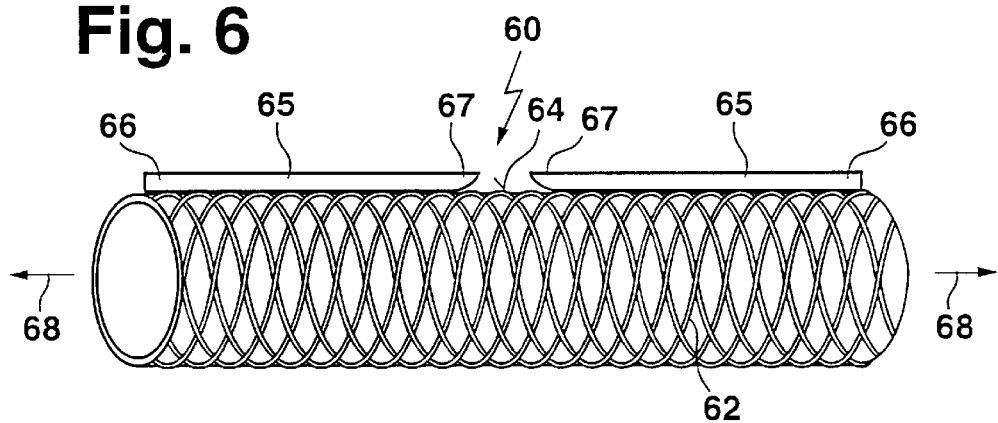
FIG. 6 shows a stent having anchors introduced on the outer surface in the extended state.

FIG. 6 shows another embodiment of a stent 60, in the elongated state, which has, a weave 62. Anchors 65 are introduced on a flat section of outer surface 64 of the stent 66. Each anchor 65 is connected to the outer surface 64 of the stent 60 in a position-stable manner via first end 66. A second end 67 seats on the outer surface 64 of the stent 60. The stent 60 is elongated in the direction of arrow 68.

Figure 7:
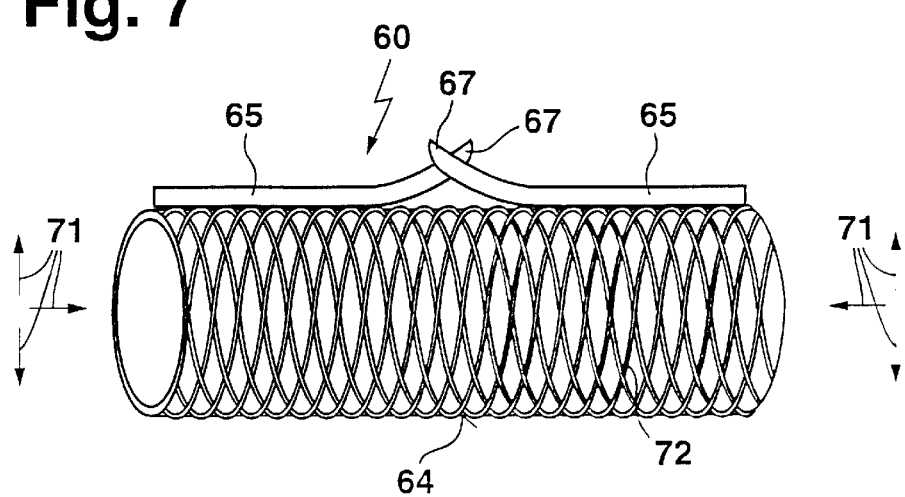
FIG. 7 shows a stent in accordance with FIG. 6 in an expanded state.

FIG. 7 shows the stent 60 of FIG. 6 in an expanded state. The stent 60 expands in the direction of arrow 71 so that an increased lumen 72 results. During expansion, the second ends 67 of the anchors 65 "stand up" and become separated from the outer surface 64. The second ends 67 facilitate the hooking or digging of the anchors 65 of the stent 60 into an adjacent surface.

Figure 8:
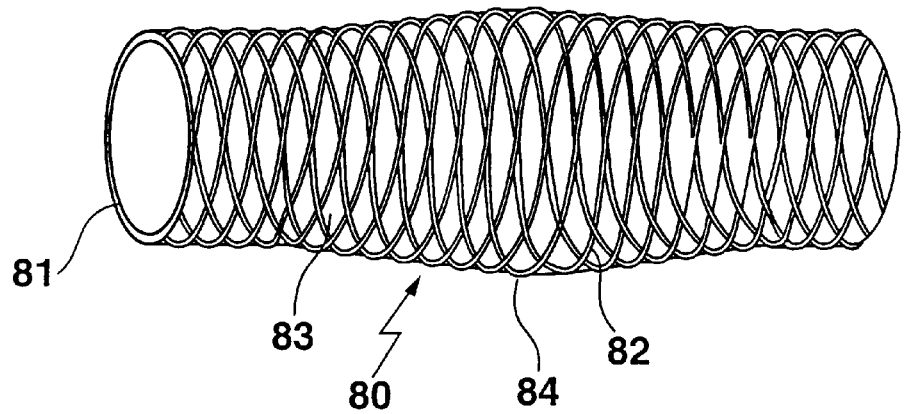
FIG. 8 shows a stent having differing surface contours in dependence on axial and radial directions.

FIG. 8 shows a stent 80 which likewise consists essentially of a tube 81, a weave 82 and a coating 83. The shape of the stent 80 differs in dependence on its axial and radial dimensions. The stent 80 assumes a distended shape 84 in an expanded state. The distended shape 84 is effected by weaving the weave 82 over a mould having this distended contour 84. The shape can be arbitrary and can be adjusted to the application. The distended shape 64 shown in FIG. 4 can be fashioned in a permanent manner using thermal shaping techniques.

Figure 9:
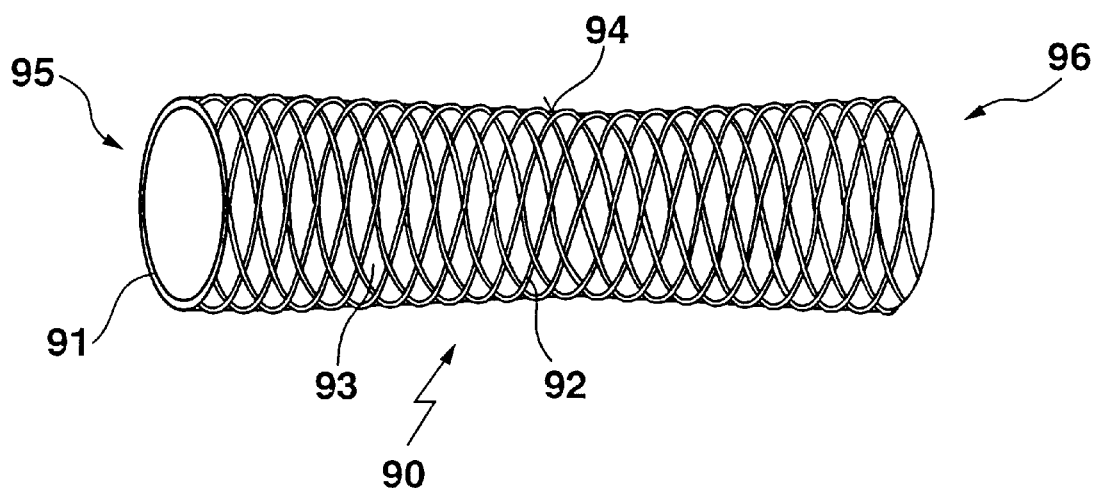
FIG. 9 shows a stent in an expanded state having widened lumens at each free end region.

FIG. 9 shows an additional embodiment of a stent 90, consisting essentially of a tube 91 supporting a weave 92 a covered by a coating 93. As seen from the side, the outer shape of the stent 90 has a concave dependence 94 along its axial extent so that the stent 90 has free ends 95, 96 which define a wider lumen in both end regions of the stent 90. The free ends 95, 96 can be reenforced by means of ring structures on the outer surface of the stent 90. These ring structures can also be introduced on arbitrary sections of the stent at the outer surface thereof independent of the embodiment of FIG. 9.

The invention concerns a stent 1 for the bracing and/or holding-open of a body cavity having a tube 2 made from an elastic material, a tubular weave 13 comprising filaments 5 seating in close adjacency to the outer surface of the tube 2 as well as a coating 4 applied to the outer surface of the tube 2 which attaches the weave 3 to the outer surface of the tube 2. The coating 4 is adapted to have a structured outer surface dominated by the weave 3. The stent 1 in accordance with the invention can be produced economically with adjustable restoring forces and facilitates a secure placing within a body cavity. Means for preventing drifting within the body cavity can also be introduced onto the outer surface of the stent.

We claim:

1. A stent system for the splitting and holding open of a body cavity, the stent system having a stent comprising:
   a tube made from an elastic material;
   a tubular weave seating firmly on an outer surface of said tube, said weave having a filament with a diameter and;
   a coating covering said tube and said weave to hold said weave on said tube, said coating having a thickness less than said filament diameter, said coating consisting essentially of a self-solidifying fluid into which said tube and said weave are dipped, whereby the stent has a structured outer surface defined by said weave, and further comprising an application device for introducing the stent into a body cavity, said application device comprising a capture and a displacement device, an application bushing, and a conical plug.

2. The stent of claim 1, wherein said weave is expanded.

3. The stent of claim 1, wherein said filament has a rounded cross section.

4. The stent of claim 1, wherein said filament comprises at least one of polyester, kevlar, fiber glass and metal.

5. The stent of claim 1, wherein said filament is impervious to x-rays.

6. The stent of claim 1, wherein at least one of said tube and said coating contain metal.

7. The stent of claim 1, wherein at least one of said tube and said coating contain silicon.

8. The stent of claim 1, wherein said filament has a fixed end, and wherein said filament comprises a plurality of threads having neighboring ends pair-wise welded to each other.

9. The stent of claim 1, wherein said weave has a shape produced by thermal shaping techniques.

10. The stent of claim 1, wherein said capture and displacement device has a substantially conical spread-out end.

11. The stent of claim 1, wherein said capture and displacement device for displacement into a lumen of said application bushing.

12. The stent of claim 1, wherein said capture and displacement device has a lumen.

13. A stent system for the splitting and holding open of a body cavity, the stent system having a stent comprising:

a tube made from an elastic material;

a tubular weave seating firmly on an outer surface of said tube, said weave having a filament with a diameter and;

a coating covering said tube and said weave to hold said weave on said tube, said coating having a thickness less than said filament diameter, said coating consisting essentially of a self-solidifying fluid into which said tube and said weave are dipped, whereby the stent has a structured outer surface defined by said weave, wherein said filament has a fixed end, and wherein said filament comprises a plurality of threads having neighboring ends pair-wises connected to each other, and further comprising a covering element for pair-wise connecting said neighboring ends.

14. The stent of claim 13, wherein said covering element comprises a covering cap pair-wise connecting said neighboring ends.

15. The stent of claim 13, wherein said covering element comprises a filament tube capturing said neighboring ends.

16. The stent of claim 8, wherein said neighboring ends are welded together.

17. A stent system for the splitting and holding open of a body cavity, the stent system having a stent comprising:

a tube made from an elastic material;

a tubular weave seating firmly on an outer surface of said tube, said weave having a filament with a diameter and;

a coating covering said tube and said weave to hold said weave on said tube, said coating having a thickness less than said filament diameter, said coating consisting essentially of a self-solidifying fluid into which said tube and said weave are dipped, whereby the stent has a structured outer surface defined by said weave, and further comprising raised portions protruding beyond said structured outer surface.

18. The stent of claim 17, wherein said raised portions consist essentially of free ends of second filament pieces extending proximate said filament.

19. The stent of claim 9, wherein said raised portions consist essentially of anchors which seat flatly on said outer surface of the stent in an elongated state of the stent and are firmly attached in a fixed spatial location at a first end thereof to said outer surface of the stent and which are separated from said outer surface of the stent at a second free end thereof in an expanded state of the stent.

20. A stent system for the splitting and holding open of a body cavity, the stent system having a stent comprising:

a tube made from an elastic material;

a tubular weave seating firmly on an outer surface of said tube, said weave having a filament with a diameter and;

a coating covering said tube and said weave to hold said weave on said tube, said coating having a thickness less than said filament diameter, said coating consisting essentially of a self-solidifying fluid into which tube and said weave are dipped, whereby the stent has a structured outer surface defined by said weave, wherein said tube has a fold-over covering an end of said filament.

21. A stent system for the splitting and holding open of a body cavity, the stent system having a stent comprising:

a tube made from an elastic material;

a tubular weave seating firmly on an outer surface of said tube, said weave having a filament with a diameter and;

a coating covering said tube and said weave to hold said weave on said tube, said coating having a thickness less than said filament diameter, said coating consisting essentially of a self-solidifying fluid into which said tube and said weave are dipped, whereby the stent has a structured outer surface defined by said weave, wherein said filament comprises a plurality of threads having at least one of differing separations with respect to each other and differing diameters.

22. A stent system for the splitting and holding open of a body cavity, the stent system having a stent comprising:

a tube made from an elastic material;

a tubular weave seating firmly on an outer surface of said tube, said weave having a filament with a diameter and;

a coating covering said tube and said weave to hold said weave on said tube, said coating having a thickness less than said filament diameter, said coating consisting essentially of a self-solidifying fluid into which said tube and said weave are dipped, whereby the stent has a structured outer surface defined by said weave, wherein said weave has shapes differing in at least one of an axial and a radial direction.

23. A method for introduction of a stent system into a body cavity, the method comprising the steps of:

a) pulling the stent into a lumen of an application bushing using a conically widening end of a capture and displacement device;

b) fixing the stent within said lumen of said application bushing using a conical plug;

c) separating said capture and displacement device from the stent;

d) pulling said capture and displacement device out of said lumen of said application bushing;

e) separating said conical plug from said application bushing;

f) turning around said capture and displacement device;

g) inserting said capture and displacement device once more into said lumen of said application bushing;

h) displacing optical means through a lumen of said capture and displacement device;

i) introducing said application bushing into the body cavity;

j) positioning the stent out of said application bushing and into the body cavity using said capture and displacement device.

* * * * *

UNITED STATES PATENT AND TRADEMARK OFFICE
Certificate

Patent No. 6,162,244                      Patented: December 19, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael Braun, Backnang, Germany; Armin Singvogel, Remseck, Germany; Walter Klepetko, Vienna, Austria; Christoph Bolliger, Oberwil, Switzerland; Lutz Freitag, Hemer, Germany; and Klaus Schmitt, Remshalden-Grunbach, Germany.

Signed and Sealed this Eighth Day of August 2006.

CORRINE M. MCDERMOTT
*Supervisory Patent Examiner*
*Art Unit 3738*